United States Patent [19]

Waller et al.

[11] Patent Number: 4,782,101
[45] Date of Patent: Nov. 1, 1988

[54] PREVENTION OF OUTGASSING IN POLYVINYLSILOXANE ELASTOMERS BY THE USE OF FINELY DIVIDED PLATINUM BLACK

[75] Inventors: Duncan E. Waller, Ypsilanti; Laurie D. Lovshe, Plymouth, both of Mich.

[73] Assignee: Manufacturers Hanover Trust Company, New York, N.Y.

[21] Appl. No.: 27,499

[22] Filed: Mar. 25, 1987

Related U.S. Application Data

[63] Continuation-in-part of Ser. No. 932,246, Nov. 19, 1986, abandoned.

[51] Int. Cl.$^4$ .................................................. A61K 6/00
[52] U.S. Cl. ..................................... 523/120; 526/279; 526/266; 526/108; 526/241; 526/112; 524/308; 524/314; 524/317
[58] Field of Search ................ 523/120; 526/279, 266, 526/108, 241, 112; 524/308, 314, 317

[56] References Cited

U.S. PATENT DOCUMENTS 4,020,014  4/1977  Service et al. ................ 252/511
4,657,959  4/1987  Bryan ........................... 524/266

FOREIGN PATENT DOCUMENTS 0046907  8/1981  European Pat. Off. .
0117056  1/1984  European Pat. Off. .

OTHER PUBLICATIONS

The Effect of Selected Surfactants on the Wetting Behavior of Gypsum Due Stone on Impression Materials–Lacy, et al., CDA Journal, Nov. 1977.
Chemie Lexikon–H. Romp; pp. 3952-3953.

Primary Examiner—Joseph L. Schofer
Assistant Examiner—Peter D. Mulcahy
Attorney, Agent, or Firm—Marjama & Pincelli

[57] ABSTRACT

A polyvinylsolixane catalyst paste which comprises up to 20,000 ppm of finely divided platinum black which functions to adsorb hydrogen gas generated in the reaction of said catalyst paste when mixed with a base paste containing hydrofunctional polydimethylsiloxane, said base paste further containing a hydrophilic surfactant.

7 Claims, No Drawings

PREVENTION OF OUTGASSING IN POLYVINYLSILOXANE ELASTOMERS BY THE USE OF FINELY DIVIDED PLATINUM BLACK

RELATED APPLICATIONS

This application is a continuation-in-part of application Ser. No. 932,246, filed Nov. 19, 1986 now abandoned.

BACKGROUND OF THE INVENTION

The liberation of small quantities of hydrogen gas from RTV addition cured polyvinylsiloxane elastomers, due to the reaction between the platinum catalyst and hydrofunctional polydimethylsiloxane, is a recognized problem. The evolution of the hydrogen gas results in the formation of pores in the model formed from the impression, producing an undesirable pitted surface.

In the U.S. Pat. No. 4,273,902, issued June 16, 1981, and assigned to G-C Dental Industrial Corp., of Tokyo, this problem is well described and a solution is claimed using 0.5 ppm or more finely divided palladium and/or a finely divided palladium alloy containing 10% by weight or more of palladium, without inhibiting the addition reaction. In Column 3, line 33 et seq., various other elemental metals are cited, including platinum, but are stated to be inferior to palladium and fail to eliminate the undesirable pores in the surface of the resulting model.

The adsorption of hydrogen by palladium is variously quoted as 502, 935 and even 2952 times its own volume, J. W. Mellor, Inorganic Chemistry Vol XVII 1947, page 616 et seq., while the adsorption of hydrogen by platinum black is quoted as 310 volumes in Vol. XVI. It therefore becomes apparent that these adsorption variabilities arise from differences in the available surface areas of the finely divided metals, but are not significant in the case of the polyvinylsiloxane elastomer application, since if sufficiently finely divided and present in adequate concentration, the adsorption saturation level will never be reached.

Another problem associated with polyvinylsiloxane dental impression materials is their extremely hydrophobic characteristics which lead to comparatively large bubble shaped artifacts in the surface of such impressions.

SUMMARY OF THE INVENTION

Accordingly, it has been discovered that when samples of extremely finely divided platinum black were obtained with the highest possible surface area, specifically 24 $M^2$/gram, and were compared with equal weight percent concentrations of palladium black, by incorporation in identical polyvinylsiloxane elastomer pastes they were found to be equally and completely effective, down to a concentration level of about 0.2 ppm by weight. An effective concentration range for the platinum black is about 0.2 to 20,000 ppm by weight. The size range for the platinum black should be as small as possible. A preferred size range for the platinum black is from about 18 to 28 Angstrom Units.

The use of platinum black in conjunction with the present invention is in controlling or preventing outgassing in all addition cured polyvinylsiloxane elastomers which are primarily used in making dental impressions.

The platinum black is used to adsorb gaseous hydrogen generated during the curing reaction, and generally at a concentration level of about 0.2 to 20,000 ppm. A preferred concentration range is from about 0.001 to 0.01 weight percent (i.e., 1,000 to 10,000 ppm). The platinum black is added or blended with the catalyst paste in any convenient manner such as illustrated in U.S. Pat. No. 4,273,902 which is incorporated herein by reference.

It has also been discovered that in a preferred embodiment of the invention that the extremely hydrophobic characterisitcs of polyvinylsiloxane dental impression materials, which lead to comparatively large bubble shaped artifacts in the surface of such impressions, can be overcome by the incorporation of relatively small quantities of selected surfactants.

DETAILED DESCRIPTION OF THE INVENTION

Both base and catalyst pastes contain vinyl polydimethyl siloxane and silica or other similar inert filler(s) and the base paste contains a moiety of hydrofunctional-polydimethylsiloxane whereas the catalyst contains both a chloroplatinic acid catalyst complex and platinum black, to adsorb any gaseous hydrogen formed during mixing of the pastes and curing of the impression.

A cured impression is produced by mixing the base paste and catalyst such as that illustrated by Example I, in a 1:1 or other suitable ratio to form a homogeneous plastic mass which is applied over the dentition and adjacent gingival tissue and allowed to cure during a time frame of several minutes prior to mouth removal. Models were made from impressions taken with the platinum black containing impression materials immediately after mouth removal and found to be free of pores in all cases at or above the 0.005 weight percent platinum level.

Impressions and resulting molds or models formed using the concept of the present invention result in a surface smoothness which is significantly better than those formed without the use of platinum black.

Another problem associated with polyvinylsiloxane dental impression materials of this invention is their extremely hydrophobic characteristics which lead to comparatively large bubble shaped artifacts in the surface of such impressions.

U.S. Pat. No. 4,600,751 teaches the controlled release of bioactive agents, and serves to demonstrate the synthesis of silicone based prepolymers which are extremely hydrophilic.

In dentistry, impression materials, particularly for making crown and bridge impressions, require a high degree of dimensional stability to facilitate the production of extremely accurate prostheses, for which the techniques of U.S. Pat. No. 4,600,751 would be totally unsuitable because high water sorption is consistent with swelling and distortion of these polymers. Furthermore there are, other definite advantages to dental impressions with low water sorption, such as ease of disinfection and sterilization.

With respect to the problem associated with the hydrophobic characteristics of the dental impression materials of the present invention is has been found possible to utilize several species of hydrophilic compounds as low concentration additives to conventional, extremely hydrophobic, addition-cured polyvinylsiloxane dental impression materials to impart truly hydrophilic surface characteristics to these materials. This results in the prevention of comparitively large bubble shaped artifacts in the surface of these impressions, due to the effects of surface tension at a strongly hydrophobic/hydrophilic interfere causing a film of moisture to form water droplets.

In a preferred embodiment of this invention, any one or more of the following surfactant type compounds are added to conventional addition-cured polyvinylsiloxane dental impression materials in relatively low concentrations of about 1.0% to 10.0% by weight.

| COMPOUND NAME | CAS NO. WHERE KNOWN |
| --- | --- |
| n-Dodecyl, Tetradecyl, Hexadecyl Alcohol Ethoxylate | 68551-12-2 |
| Polyethylene Glycol Monolaurate | 9004-81-3 |
| Polyethylene Glycol Dilaurate | |
| Polyethylene Glycol Monoleate | |
| Polyethylene Glycol Dioleate | |
| Polyethylene Glycol Monotallate | |
| Polyethylene Glycol Ditallate | |
| Sorbitan Monolaurate | |
| Sorbitan Monoleate | |
| Sorbitan Trioleate | |
| Sorbitan Monotallate | |
| Sorbitan Tritallate | |
| Polyethylene Glycol Glycerol Cocoeate | |
| Caprylic Triglyceride | |
| Polyoxyethylene Tridecyl Alcohol | 24938-91-8 |
| Polyoxyethylene Lauryl Ether | 5274-68-0 |
| Nonylphenoxypoly (ethyleneoxy) ethanol | 9016-45-9 |
| Polyoxyethylene Sorbitan Monolaurate | |
| Sorbitan Monolaurate Polyoxyethylene Polysorbate | 9005-64-5 |
| Polyoxyethylene Oleyl Alcohol | |

The above listing of suitable surfactants is not exhaustive, but serves to illustrate twenty representative examples of the manny chemical permutations possible with the family of Polyol fatty acid ester and ethoxylated ester type surfactants useful for this invention.

The effectiveness of these surfactant additives is readily apparent in their ability to reduce the aqueous contact angle with cured or uncured addition-cured polyvinylsiloxane dental impression materials from the range of 95°-110° down to 30° or less. Upon contact of the dental impression materials with the dentition and gingiva any moisture present on the surface of these oral tissues is readily miscible with the surfactant moiety available at the surface of the impression material, which provides uniform wetting of the interface between the impression material and the oral tissues, thereby dramatically reducing surface tension.

The following example illustrates one embodiment of the present invention. The concentrations are in weight percent unless otherwise stated.

EXAMPLE I

Embodiments of Platinum Black for gaseous adsorption

| BASE PASTE (VERY HEAVY VISCOSITY) | WT % | CATALYST PASTE (VERY HEAVY VISCOSITY) | WT % |
| --- | --- | --- | --- |
| Vinyl Polydimethylsiloxane | 20% | Vinyl Polydimethysiloxane | 20% |
| Hydropolydimethyl Siloxane | 3% | *Cyclic Vinyl Siloxane | 0.4% |
| Silica Filler | 70% | **Chloroplatinic Acid Complex | 1.0% |
| Liquid Petroleum or other inert plasticizer | 7% | Liquid Petroleum or other inert plasticizer | 7% |
| | | Silica or other inert filler | 71.6% |

The following illustrates suitable compositional ranges for the components of the base and catalyst paste.

| BASE PASTE | WT % | CATALYST PASTE | WT % |
| --- | --- | --- | --- |
| Vinyl Polydimethyl-siloxane | 10-60 | Vinyl Polydi-methylsiloxane | 10-60 |
| Hydropolydimethyl Siloxane | 1-10 | Cyclic Vinyl Siloxane | 0-2 |
| Silica Filler | 20-80 | Chloroplatinic Acid Complex | 0.1-5.0 |
| Liquid Petroleum | 0-15 | Platinum Black | 0.2-20,000 ppm |
| | | Plasticizer | 0-15 |
| | | Filler | 20-80 |

The following illustrates suitable compositional ranges for a cured dental impression material of the present invention.

| VERY HEAVY VISCOSITY MATERIAL (PUTTY) | WT % |
| --- | --- |
| Vinyl Polydimethylsiloxane | 10-60 |
| Cyclic Vinyl Siloxane | 0-1 |
| Hydropolydimethyl Siloxane | 0.5-5.0 |
| Filler | 20-80 |
| Chloroplatinic Acid Complex | 0.05-2.5 |
| Platinum Black | 0.1-10,000 ppm |
| Plasticizer | 0-15 |
| Surfactant (optional but preferred) | 2-10 |

*Available under the tradename PSW 2204 from Petrarch Silicones of Bristol, PA.
**Available under the tradename PSW 2206 from Petrarch Silicones of Bristol, PA.

Embodiments using surfactants to confer hydrophilic characteristics:

EXAMPLE 2

| Low viscosity Catalyst paste with surfactant | WT % |
| --- | --- |
| Vinyl functional polydimethylsiloxane | 51.785 |
| Silaceous Filler | 43.0 |
| n-Dodecyl, Tetradecyl, Hexadecyl Alcohol Ethoxylate | 4.0 |
| Pigment | 1.0 |
| Cyclic vinyl functional prepolymer | 0.2 |
| Chloroplatinic acid catalyst complex | 0.01 |
| Platinum Black | 0.005 |
| | 100.00 |

Excellent hydrophilic surface characteristics, but unpleasant taste.

EXAMPLE 3

| Low viscosity Base paste with surfactant | |
| --- | --- |
| Vinyl functional polydimethlsiloxane | 46.0 |
| Silaceous Filler | 42.0 |
| Hydrofunctional Polydimethylsiloxane | 7.0 |
| Pigment | 2.0 |
| Nonylphenoxypoly(ethyleneoxy)ethanol | 3.0 |

-continued

| Low viscosity Base paste with surfactant | |
|---|---|
| | 100.0 |

Excellent hydrophilic surface characteristics and acceptable taste.

EXAMPLE 4

| Low viscosity Base paste with surfactant | |
|---|---|
| Vinyl functional polydimethylsiloxane | 46.0 |
| Silaceous Filler | 41.0 |
| Hydrofunctional polydimethylsiloxane | 7.0 |
| n-Dodecyl, Tetradecyl, Hexadecyl Alcohol Ethoxylate | 4.0 |
| Pigment | 2.0 |
| | 100.00 |

Excellent hydrophilic surface characteristics, but unpleasant taste.

Although the above examples are restricted to low viscosity polyvinylsiloxane dental impression materials the same family of Polyol fatty acid ester and ethoxylated ester type surfactant can be used as additives in the regular and heavy, even putty viscosities of the same type of material with equally effective results.

The following illustrates suitable compositional ranges for the components of the base and catalyst pastes of Examples 2 through 4.

| BASE PASTES | WT % | CATALYST PASTES | WT % |
|---|---|---|---|
| Vinyl polydimethylsiloxane | 25–75 | Vinyl Polydimethylsiloxane | 25–75 |
| Hydropolydimethyl siloxane | 1–12 | Cyclic Vinyl Siloxane | 0.5 |
| Silaceous Filler(s) | 25–75 | Silaceous Filler(s) | 25–72 |
| Surfactant(s) | 1–10 | Surfactant(s) | 1–10 |
| Pigment(s) | 0.5 | Pigment(s) | 0.5 |
| | | Chloroplatinic Acid Complex | 0.1–5.0 |
| | | Platinum Black | 0.2–20,000 ppm |

The following illustrates suitable compositional ranges for a cured dental impression material of Examples 2 through 4 of the present invention:

| LOW VISCOSITY MATERIAL (LIGHT BODY OR WASH) | WT % |
|---|---|
| Vinylpolydimethylsiloxane | 25–75 |
| Hydro polydimethylsiloxane | 0.5–5.0 |
| Cyclic Vinyl siloxane | 0–1 |
| Silaceous Filler(s) | 25–75 |
| Surfactant(s) | 1–10 |
| Pigment(s) | 0–5 |
| Chloraplatinic Acid Complex | 0.05–2.5 |
| Platinum Black | 0.01–10,000 ppm |

The following is a preferred embodiment of the present invention which exhibits the desired properties with respect to controlling outgassing and hydrophilic characteristics:

| | WT % |
|---|---|
| LOW VISCOSITY BASE PASTE WITH SURFACTANT | |
| Vinyl functional polydimethylsiloxane (4000 cps) | 46.0 |
| Calcium Silicate Filler | 42.0 |
| Hydrofunctional polydimethylsiloxane | 7.0 |
| Nonylphenoxypoly (ethyleneoxy) ethanol | 3.0 |
| Cobalt Blue Pigment | 2.0 |
| | 100.00 |

| | WT % |
|---|---|
| LOW VISCOSITY CATALYST PASTE WITH PLATINUM | |
| Vinyl functional polydimethylsiloxane (4000 cps) | 54.73 |
| Calcium Silicate Filler | 43.98 |
| Cobalt Blue Pigment | 1.0 |
| Cyclic Vinyl functional prepolymer | 0.27 |
| Chloroplatinic Acid Catalyst complex | 0.01 |
| Platinum Black (24 $M^2$/gm) | 0.01 |
| | 100.00 |

The following is a typical method used in preparing the compounds of the present invention. Other methods and compounds, such as those set forth in the above mentioned U.S. Pat. No. 4,273,902 may also be used in conjunction with this invention and are incorporated herein by reference.

BASE PLATE

Blend together in a double planetary mixer the three liquid components, Vinyl functional polydimethylsiloxane, Hydrofunctional polydimethylsiloxane and Nonylphenoxypoly(ethyleneoxy)ethanol. Add pigment, and then reblend to evenly disperse the pigment, filler is then added and mixed until thoroughly homogenous to form a low viscosity fluid paste. The resulting paste is then rollmilled to maximize homogeneity followed by packaging as desired.

CATALYST PASTE

Preblends are made of the Chloroplatinic acid complex with a portion of the Vinyl functional polydimethylsiloxane and of the Platinum Black with a portion of the Calcium Silicate filler. Blend together the three liquid components, Catalyst complex preblend, balance of Vinyl functional polydimethylsiloxane and Cyclic Vinyl prepolymer. Add pigment, reblend to disperse, then add Platinum Black preblend, followed by balance of the filler and mix until throughly homogenous. Rollmill to maximize homogeneity and then package as desired.

While the invention has been described in detail with respect to specific embodiments thereof, it will be understood by those skilled in the art that variations and modifications may be made without departing from the essential features thereof.

What is claimed is:

1. A two component dental impression material which comprises the following:

| BASE PASTE | WT % | CATALYST PASTE | WT % |
|---|---|---|---|
| Vinyl Polydimethyl-siloxane | 10–60 | Vinyl Polydi-methylsiloxane | 10–60 |
| Hydropolydimethyl Siloxane | 1–10 | Cyclic Vinyl Siloxane | 0–2 |
| Silica Filler | 20–80 | Chloroplatinic | 0.1–5.0 |

| BASE PASTE | WT % | CATALYST PASTE | WT % |
|---|---|---|---|
| Liquid Petroleum | 0–15 | Acid Complex Platinum Black | 0.2–20,000 ppm |
| | | Plasticizer | 0–15 |
| | | Filler | 20–80 | and wherein said platinum black has a surface area of about 24 $M^2$/gram and a size range of about 18 to 28 Angstrom Units.

2. The impression material of claim 1 in which the surfactant is selected from the family of polyol fatty acid esters and ethoxylated esters.

3. The impression material of claim 1 in which the surfactant comprises nonylphenoxypoly(ethyleneoxy)ethanol.

4. The impression material of claim 1 in which the surfactant comprises at least one compound selected from the group comprising:
   n-Dodecyl, Tetradecyl, Hexadecyl Alcohol Ethoxylate
   Polyethylene Glycol Monolaurate
   Polyethylene Glycol Dilaurate
   Polyethylene Glycol Monoleate
   Polyethylene Glycol Dioleate
   Polyethylene Glycol Monotallate
   Polyethylene Glycol Ditallate
   Sorbitan Monolaurate
   Sorbitan Monoleate
   Sorbitan Trioleate
   Sorbitan Monotallate
   Sorbitan Tritallate
   Polyethylene Glycol Glycerol Cocoeate
   Caprylic Triglyceride
   Polyoxyethylene Tridecyl Alcohol24938-91-8
   Polyoxyethylene Lauryl Ether5274-68-0
   Nonylphenoxypoly(ethyleneoxy)ethanol9016-45-9
   Polyoxyethylene Sorbitan Monolaurate
   Sorbitan Monolaurate Polyoxyethylene Polysorbate
   Polyoxyethylene Oleyl Alcohol.

5. A cured dental impression which comprises the following composition:

| | WT % |
|---|---|
| Vinyl Polydimethylsiloxane | 10–60 |
| Cyclic Vinyl Siloxane | 0–1 |
| Hydropolydimethyl Siloxane | 0.5–5.0 |
| Filler | 20–80 |
| Chloroplatinic Acid Complex | 0.05–2.5 |
| Platinum Black | 0.1–10,000 ppm |
| Plasticizer | 0–15 |
| Surfactant | 1–10 | and wherein said platinum black has a surface area of about 24 $M^2$/gram and a size range of about 18 to 28 Angstrom Units.

6. A polyvinylsiloxane catalyst paste which comprises up to 20,000 ppm of finely divided platinum black which functions to absorb hydrogen gas generated in the reaction of said catalyst paste when mixed with a base paste containing hydrofunctional polydimethylsiloxane, said base paste further containing a hydrophilic surfactant selected from the family of polyol fatty acid esters and ethoxylated esters and wherein said platinum black has a surface area of about 24 $M^2$/gram and a size range of about 18 to 28 Angstrom Units.

7. The composition of claim 6 in which the surfactant comprises at least one compound selected from the group consisting of:
   n-Dodecyl, Tetradecyl, Hexadecyl Alcohol Ethoxylate
   Polyethylene Glycol Monolaurate
   Polyethylene Glycol Dilaurate
   Polyethylene Glycol Monoleate
   Polyethylene Glycol Dioleate
   Polyethylene Glycol Monotallate
   Polyethylene Glycol Ditallate
   Sorbitan Monolaurate
   Sorbitan Monoleate
   Sorbitan Trioleate
   Sorbitan Monotallate
   Sorbitan Tritallate
   Polyethylene Glycol Glycerol Cocoeate
   Caprylic Triglyceride
   Polyoxyethylene Tridecyl Alcohol24938-91-8
   Polyoxyethylene Lauryl Ether5274-68-0
   Nonylphenoxypoly(ethyleneoxy)ethanol9016-45-9
   Polyoxyethylene Sorbitan Monolaurate
   Sorbitan Monolaurate Polyoxyethylene Polysorbate
   Polyoxyethylene Oleyl Alcohol.

* * * * *